(12) United States Patent
Chen (10) Patent No.: US 8,362,188 B2
(45) Date of Patent: Jan. 29, 2013

(54) FLAME-RETARDANT HARDNER FOR EPOXY RESIN AND FLAME-RETARDANT RESIN MATERIAL COMPRISING THE SAME

(76) Inventor: Chien-Hong Chen, Taichung (TW)

( * ) Notice: Subject to any disclaimer, the term of this patent is extended or adjusted under 35 U.S.C. 154(b) by 0 days.

(21) Appl. No.: 13/527,998

(22) Filed: Jun. 20, 2012

(65) Prior Publication Data

US 2012/0329960 A1    Dec. 27, 2012

(30) Foreign Application Priority Data

Jun. 24, 2011    (TW) .................................. 100122158

(51) Int. Cl.
*C08G 59/68* (2006.01)
*C07F 9/6571* (2006.01)
(52) U.S. Cl. .............................. 528/89; 558/76; 564/230
(58) Field of Classification Search .................... 528/89; 558/76; 564/230
See application file for complete search history.

(56) References Cited

U.S. PATENT DOCUMENTS 6,797,821 B2    9/2004    Wang et al.

FOREIGN PATENT DOCUMENTS

JP    3653247    5/2005
TW    593526    6/2007

*Primary Examiner* — Kristin Bianchi
(74) *Attorney, Agent, or Firm* — Stuart D. Frenkel; Frenkel & Associates, P.C.

(57) ABSTRACT

The present invention provides a flame-retardant hardener for epoxy resin having a compound represented by formula (I):

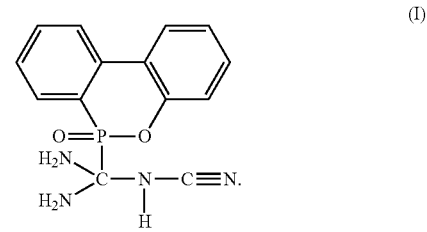

(I)

In addition, the present invention also provides a flame-retardant resin material comprising the aforementioned flame-retardant hardener for epoxy resin. Moreover, the present invention further provides a method for manufacturing a flame-retardant hardener for epoxy resin, which can be directly applied in a resin curing process after a cooling step without additional purification. As described by the present invention, the flame-retardant hardener for epoxy resin in accordance with the present invention can replace the conventional toxic halogenated resins, and provide an environmental-friendly flame-retardant hardener for epoxy resin.

11 Claims, 10 Drawing Sheets

FLAME-RETARDANT HARDNER FOR EPOXY RESIN AND FLAME-RETARDANT RESIN MATERIAL COMPRISING THE SAME

CROSS-REFERENCE TO RELATED APPLICATION

Pursuant to 35 U.S.C. §119(a), this application claims the benefit of the priority to Taiwan Patent Application No. 100122158, filed Jun. 24, 2011. The content of the prior application is incorporated herein by its entirety.

BACKGROUND OF THE INVENTION

1. Field of the Invention

The present invention relates to a flame-retardant hardener for epoxy resin and a flame-retardant resin material comprising the same, which can be applied to fields of printed circuit board material or integrated circuit (IC) packaging material, etc.

2. Description of the Prior Arts

When resins are used as a printed circuit board material and an IC packaging material, the monomer of resins are typically brominated before preparing a brominated resin in order to make the products with flame-retardant characteristics. Although the printed circuit board material and IC packaging material made of brominated resins usually have good flame-retardant characteristics, the brominated resins produce high corrosive bromine free radicals, hydrogen bromide (HBr), high toxic polybromine dibenzofurans and polybromine dibenzodioxins when being incinerated. The aforementioned substances cause a huge damage to both people and the environment.

In order to overcome the problems, a phosphorus-containing group contained in 9,10-dihydro-9-oxa-10-phosphaphenanathrene-10-oxide (abbreviated as DOPO) is attached onto the epoxy resin to provide a flame-retardant resin material, which is able to replace the toxic brominated resin. When a product made of DOPO is heated at a high temperature, the phosphorus-containing group comprised in DOPO will produce non-volatile phosphorous compounds such as phosphoric acid ($H_3PO_4$) and Poly(phosphorous acid). Because poly(phosphorous acid) has an ability of protonating organic molecules and has a strong dewaterability, and because $H_3PO_4$ can be an agglutinant of carbon for forming an insulated layer and also has a strong dewaterability, the non-volatile phosphorous compounds can make a resin material have a desired flame-retardant characteristic.

Generally, resins for printed circuit board material and IC packaging material must be synthesized with a curing agent (hardener) and followed by other processes. Based on the aforementioned means of offering a flame-retardant characteristic to resins with DOPO, a halogen-free flame-retardant printed circuit board material and IC packaging material can be also obtained by DOPO-containing curing agent.

The aforementioned hypothesis that a curing agent attached with a phosphorus-containing group of DOPO will provide a flame-retardant material has been well known in the related arts. However, a feasible and specific process and technique still have not been developed. TW patent No. 593526, JP patent No. 3653247 and U.S. Pat. No. 6,797,821 disclose a compound represented by the The compound (so-called DOPO-DICY) is obtained by attaching a phosphorus-containing group of DOPO onto a curing agent (dicyandiamide, DICY). According to the preparation method disclosed by the publications, DICY must be heated at 120° C. until completely melted. However, DICY has a high melting point about 209.5° C., it is difficult to use a conventional apparatus disclosed by the patents to perform a synthesis of DOPO-DICY. Moreover, there is still a need to develop other various curing agents for improving the technical development.

SUMMARY OF THE INVENTION

To overcome the predicaments that curing agents such as DOPO-DICY (an agent for curing materials) are difficult to be synthesized successfully, the present invention provides novel flame-retardant hardeners by attaching the phosphorus-containing group of DOPO onto the carbon of DICY. The present invention also provides a method beneficial for mass production of the flame-retardant hardener for epoxy resin.

To achieve the objective, the present invention provides a flame-retardant hardener for epoxy resin having a compound represented by formula (I):

Preferably, the flame-retardant hardener for epoxy resin further has a compound represented by formula (II):

Preferably, the flame-retardant hardener for epoxy resin further has a compound represented by formula (III):

(III)

Preferably, the flame-retardant hardener for epoxy resin further has compounds with structures represented by formulas (II) and (III).

According to the present invention, the compounds (I), (II), and/or (III) are flame-retardant hardeners which are used for curing the epoxy resin. In other words, the flame-retardant hardener for epoxy resin in accordance with the present invention does have the flame-retardant characteristics itself and makes an epoxy resin comprising the flame-retardant hardener have the flame-retardant characteristics. The present invention also provides a flame-retardant resin material comprising at least one aforementioned flame-retardant hardener for epoxy resin.

The present invention further provides a method for manufacturing a flame-retardant hardener for epoxy resin, comprising the steps of:

providing a phosphorus-containing compound, wherein the phosphorus-containing compound is 9,10-dihydro-9-oxa-10-phosphaphenanthrene-10-oxide (DOPO) having a structure represented by formula (IV):

(IV)

heating the phosphorus-containing compound until fully melted;

providing a curing agent, wherein the curing agent is dicyandiamide (DICY); and mixing the curing agent with the phosphorus-containing compound to form a mixture, and heating the mixture to undergo a reaction of DICY with DOPO for a period of time; and cooling the mixture to obtain the flame-retardant hardener for epoxy resin.

Preferably, the phosphorus-containing compound of the mixture has a mole number more than or equal to a mole number that the curing agent of the mixture has.

Preferably, the mixture is heated at a temperature higher than 130° C.

The present invention provides a flame-retardant hardener for epoxy resin with the following advantages:

1. The phosphorus-containing group of DOPO can be effectively attached to DICY. A mixture obtained from the synthesis reaction can be directly applied into a resin curing process after a cooling step without additional purification.

2. The toxic halogenated resins such as brominated resins can be largely reduced in amount and even replaced by using the flame-retardant hardener for epoxy resin in accordance with the present invention. Therefore, a flame-retardant hardener for epoxy resin and a flame-retardant resin material in accordance with the present invention are beneficial for people and the environment, and are also helpful for the technical improvements in the related fields.

Other objectives, advantages and novel features of the invention will become more apparent from the following detailed description when taken in conjunction with the accompanying drawings.

BRIEF DESCRIPTION OF THE DRAWINGS

FIG. 4 is a FTIR spectrum of a mixture obtained from a reaction of DOPO and

DICY with a molar ratio of 1:1 for 14 hours;

DETAILED DESCRIPTION OF THE PREFERRED EMBODIMENTS

Hereinafter, one skilled in the arts can easily realize the advantages and effects of a flame-retardant hardener for epoxy resin and the flame-retardant resin material comprising the same in accordance with the present invention from the following examples. Therefore, it should be understood that the descriptions proposed herein are just preferable examples only for the purpose of illustrations, not intended to limit the scope of the invention. Various modifications and variations could be made in order to practice or apply the present invention without departing from the spirit and scope of the invention.

In the specification, the following structures are respectively represented by formula (I), (II), and (III):

The compounds represented by formulas (I), (II), and (III) are synthesized from DOPO with DICY. The phosphorus-containing group of DOPO can be attached onto the carbon of DICY, and producing mixtures comprising different ratios of compounds represented by formulas (I), (II), and (III) according to different reaction conditions. The synthesis route is represented as follows:

Hereinafter, the technical means in accordance with the present invention for achieving the abovementioned objectives are illustrated from the following preferable examples and figures.

Preparation Example

Preparation of a Flame-Retardant Hardener for Epoxy Resin in Accordance with the Present Invention 1. A reaction flask equipped with an electric stirrer, a thermocouple and an adjustable thermostat heater was provided. The reaction flask might be filled with nitrogen to be isolated from the air and moisture.

2. DOPO in an appropriate amount was added into the reaction flask and heated to a temperature ranging from 120° C. and 135° C. until DOPO was fully melted.

3. DICY in an appropriate amount was added into the reaction flask to form a mixture. In this step, the reaction temperature was higher than 110° C. to ensure that DOPO of the mixture was in a molten state. In the Preparation Example, the molar ratio of DOPO to DICY was 1:1, 1.8:1 and 5:1 respectively, for analysis and comparison.

4. The reaction flask was slowly heated to 175° C. for 4 hours to 14 hours. In the Preparation Example, the reactions were respectively performed for 6 hours and 14 hours when the molar ratio of DOPO to DICY was 1:1. The reactions were respectively performed for 2 hours and 8 hours when the molar ratio of DOPO to DICY was 1.8:1. The reaction was performed for 14 hours when the molar ratio of DOPO to DICY was 5:1.

5. The mixtures obtained from the aforementioned step were subsequently cooled. Finally, the mixtures (the flame-retardant hardener for epoxy resin in accordance with the present invention) comprising three products represented by formulas (I), (II), and (III) were produced.

Test Example 1

Structural Analysis of the Flame-Retardant Hardener for Epoxy Resin in Accordance with the Present Invention In the present example, the structures of the products produced by Preparation Example were determined by $^1$H NMR and FTIR spectroscopy with reference to the $^1$H NMR spectrum of pure DOPO.

Figure 1:
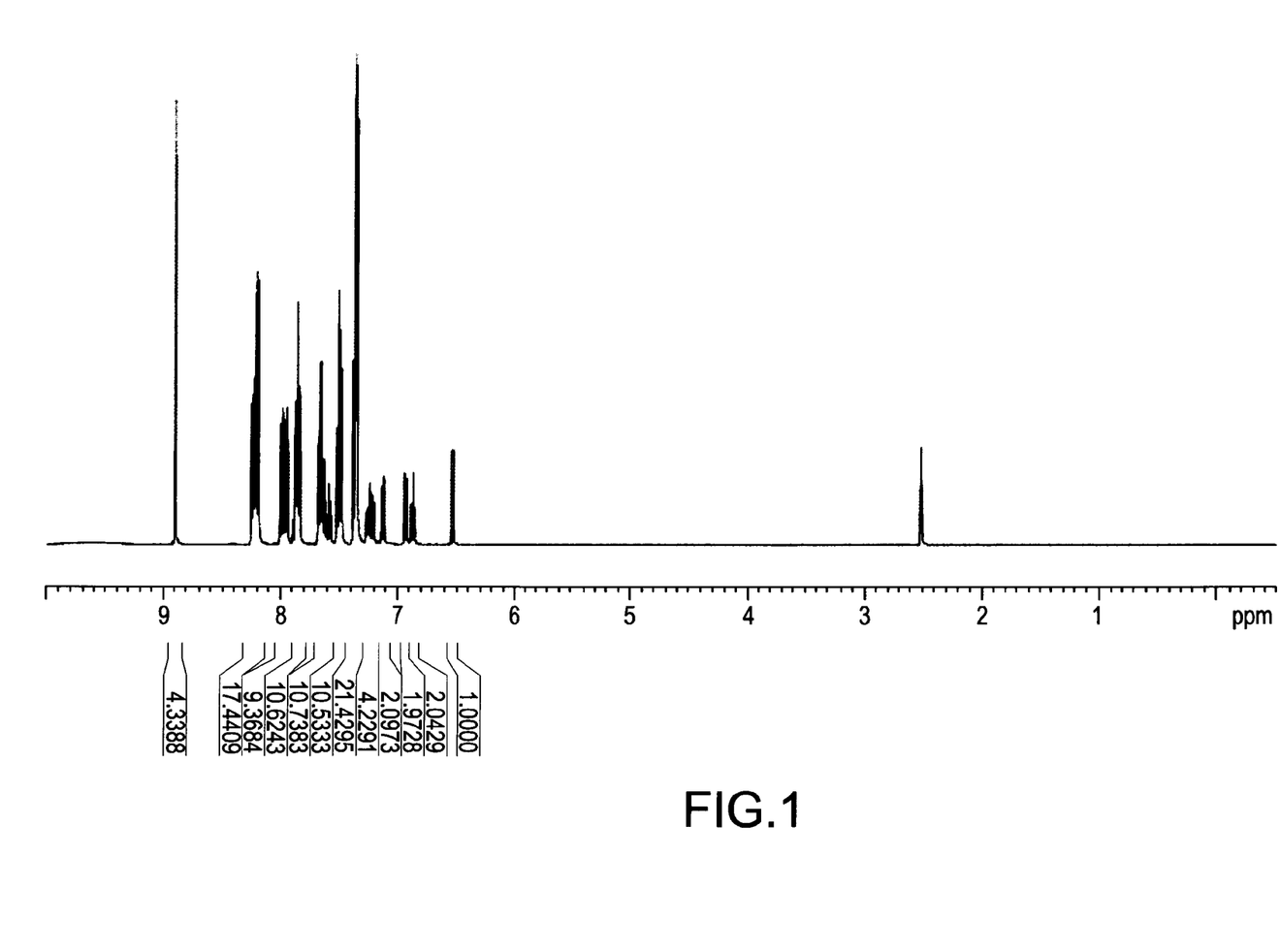
FIG. 1 is a $^1$H nuclear magnetic resonance (NMR) spectrum of pure DOPO.

FIG. 1 illustrated a $^1$H NMR spectrum of pure DOPO. The absorption in the range from δ8.85 to δ8.90 ppm (parts per million) was identified as the absorption of proton on single bond between phosphorous and hydrogen (P—H bond) in DOPO.

Figure 2:
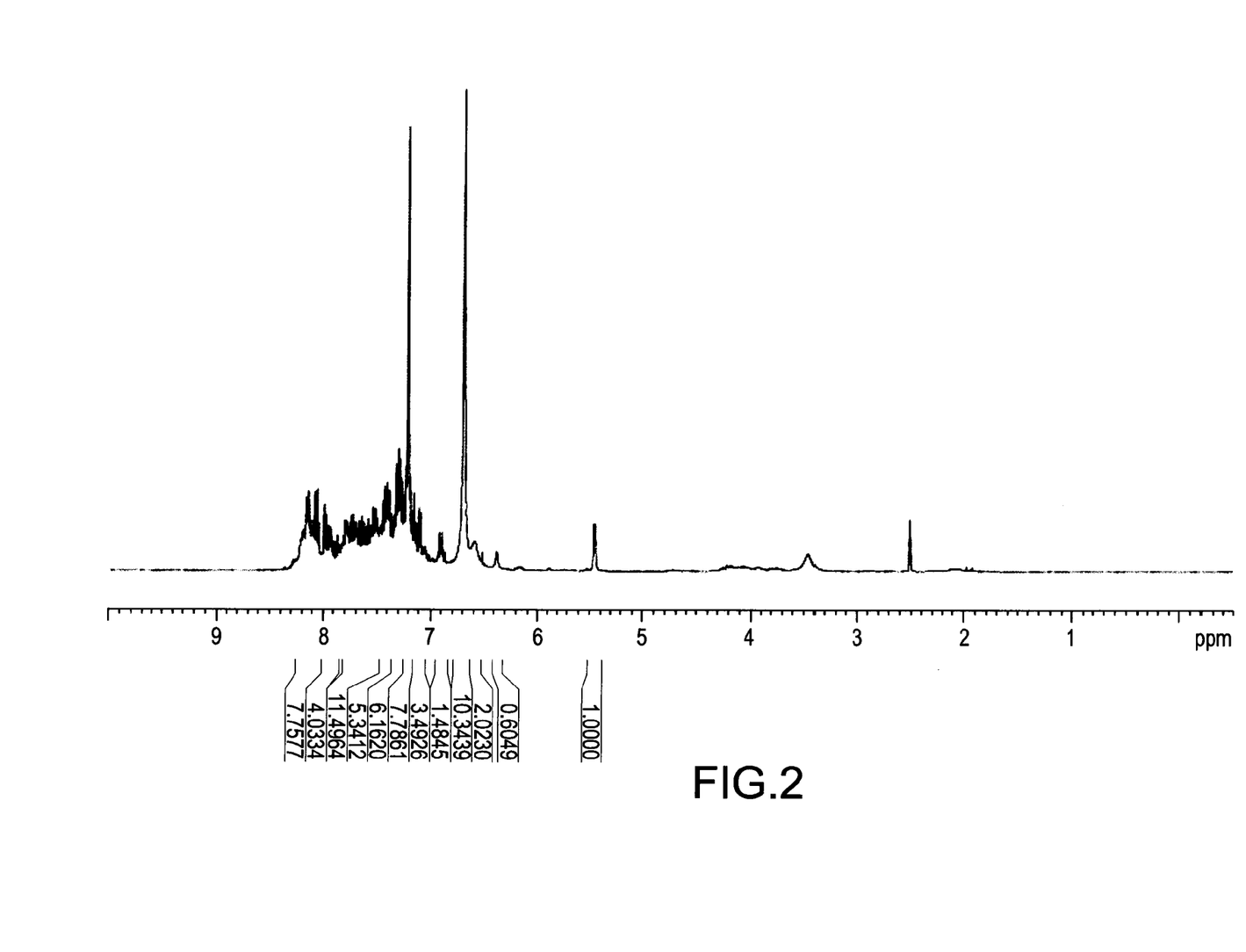
FIG. 2 is a $^1$H NMR spectrum of a mixture obtained from a reaction of DOPO and DICY with a molar ratio of 1:1 for 6 hours.
Figure 3:
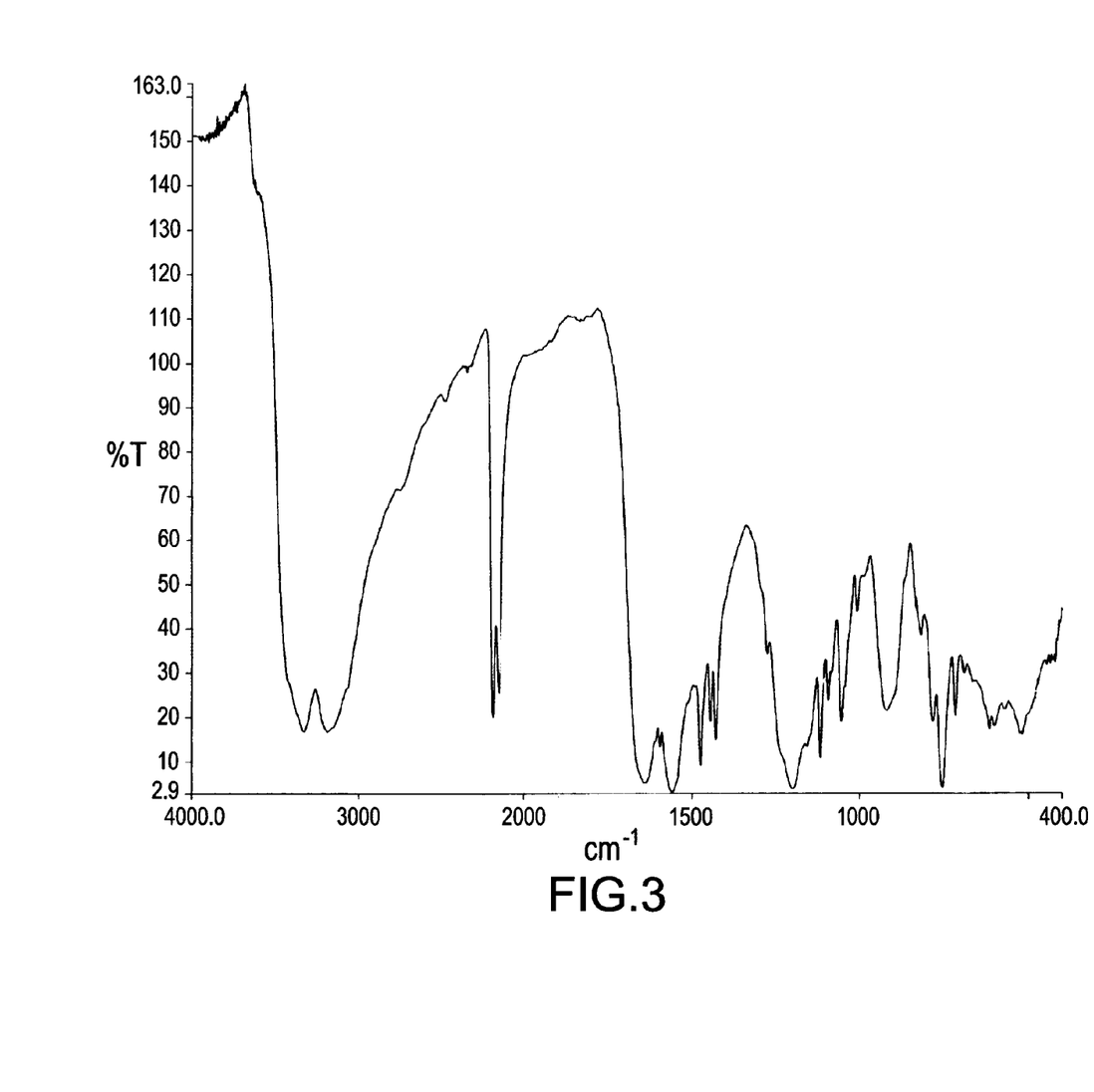
FIG. 3 is a fourier transform infrared (FTIR) spectrum of a mixture obtained from a reaction of DOPO and DICY with a molar ratio of 1:1 for 6 hours.

FIG. 2 illustrated a $^1$H NMR spectrum of a mixture obtained from a reaction of DOPO and DICY with a molar ratio of 1:1 for 6 hours. The disappearing absorption peak in the range from δ8.85 ppm to δ8.90 ppm (identified as the absorption of proton on P—H bond in DOPO) demonstrated that DOPO was completely reacted with DICY after 6 hours. The strong peaks in the range from δ6.65 ppm to δ6.69 ppm and around δ7.2 ppm were identified as the absorptions of protons on —C(NH$_2$)$_2$. With reference to FIG. 3, the chemical structure of the identical mixture with FIG. 2 obtained from a reaction of DOPO and DICY with a molar ratio of 1:1 for 6 hours was further determined by FTIR spectroscopy. According to the results from FIG. 3, the mixture had a quite apparent absorption peak in the range from 2150 cm$^{-1}$ to 2250 cm$^{-1}$ identified as triple bond between carbon and nitrogen (—C≡N bond) when DOPO was completely reacted.

Figure 4:
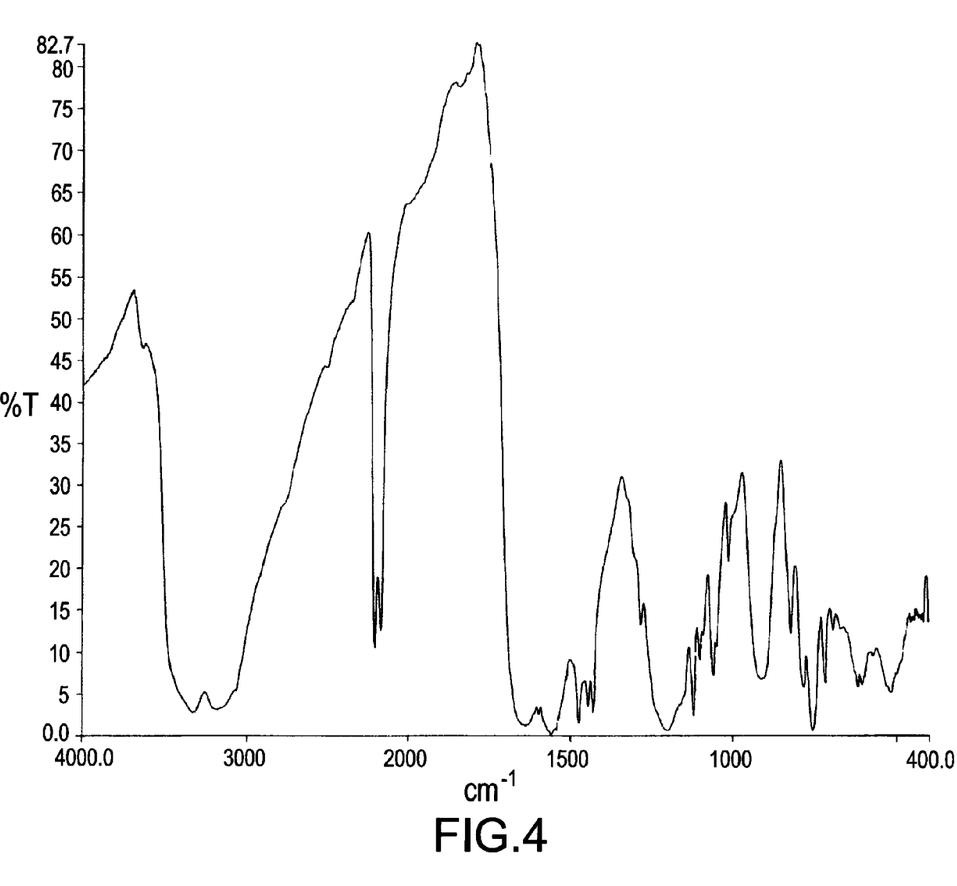

FIG. 4 illustrated a FTIR spectrum of a mixture obtained from a reaction of DOPO and DICY with a molar ratio of 1:1 for 14 hours. The mixture had a quite apparent absorption peak of —C≡N bond in the range from 2150 cm$^{-1}$ to 2250 cm$^{-1}$. According to an almost identical spectrum of FIG. 4 with FIG. 3, the spectra demonstrated that no additional reaction occurred after DOPO was completely reacted with DICY, and an amount of carbon on —C≡N bond still remained in the mixture and did not react with DOPO. It could be assumed that all phosphorus-containing groups contained in DOPOs were not specifically attached onto the carbons of —C≡N bond in DICYs.

Figure 5:
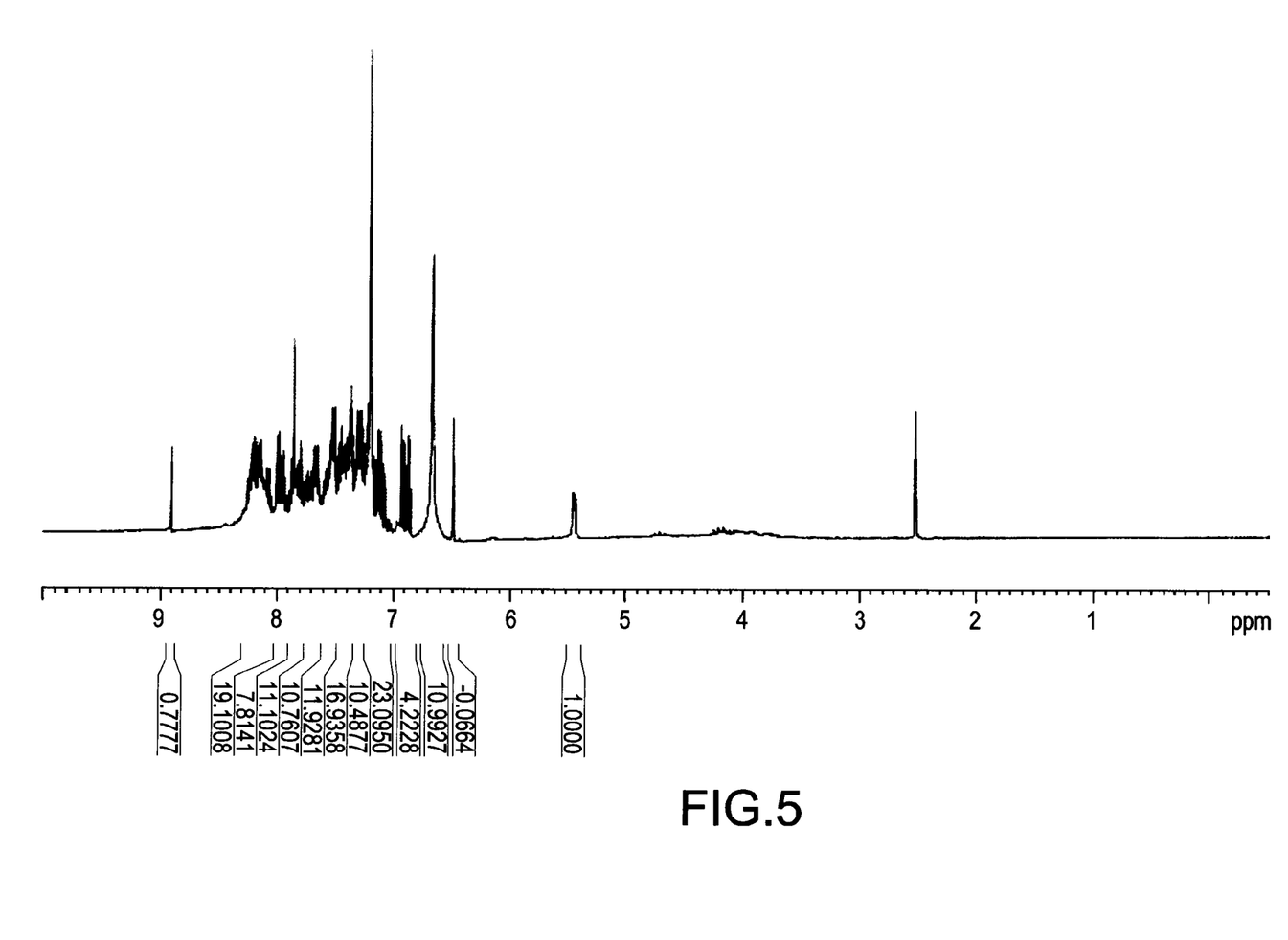
FIG. 5 is a $^1$H NMR spectrum of a mixture obtained from a reaction of DOPO and DICY with a molar ratio of 1.8:1 for 2 hours.

FIG. 5 illustrated a $^1$H NMR spectrum of a mixture obtained from a reaction of DOPO and DICY with a molar ratio of 1.8:1 for 2 hours. The absorption peak of proton on P—H bond in DOPO in the range from δ8.85 ppm to δ8.90 ppm was still quite apparent. The result showed that a lot of DOPO had not reacted with DICY. In addition, the absorption peak of proton on —C(NH$_2$)$_2$ in the range from δ6.65 ppm to δ6.69 ppm was also quite apparent. On the other hand, another absorption peak around δ7.2 ppm, also identified as an absorption of proton on —C(NH$_2$)$_2$, had clearly appeared in the $^1$H NMR spectrum. The results demonstrated that even though the reaction between DOPO and DICY had not fully completed, a portion of DOPO had already attached onto DICY.

Figure 7:
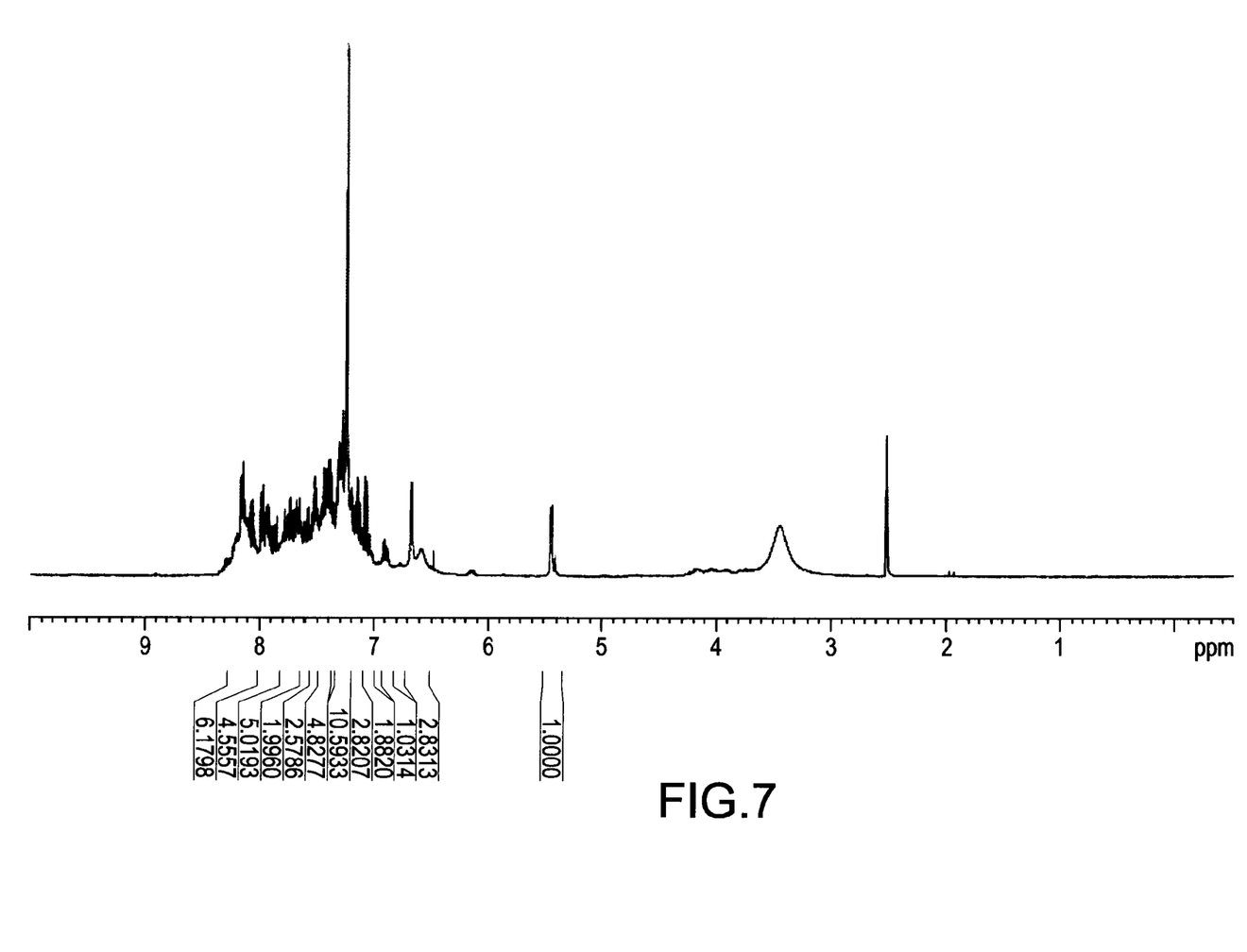
FIG. 7 is a $^1$H NMR spectrum of a mixture obtained from a reaction of DOPO and DICY with a molar ratio of 1.8:1 for 8 hours.

Furthermore, FIG. 7 illustrated a $^1$H NMR spectrum of a mixture obtained from a reaction of DOPO and DICY with a molar ratio of 1.8:1 for 8 hours. The absorption peak of proton on P—H bond in DOPO in the range from δ8.85 ppm to δ8.90 ppm disappeared, demonstrating that DOPO was fully reacted. As the reaction was proceeded for 8 hours, the weaker absorption peak of proton on —C(NH$_2$)$_2$ in the range from δ6.65 ppm to δ6.69 ppm and the stronger absorption around δ7.2 ppm demonstrated that the major products synthesized from reactants of DOPO and DICY with a molar ratio of 1.8:1 after a complete reaction was compound (III).

Comparing FIG. 5 and FIG. 7, the absorption peak of proton in the range from δ6.65 ppm to δ6.69 ppm became weaker and the absorption peak of proton around δ7.2 ppm became stronger during the reaction process of DOPO and DICY with a molar ratio of 1.8:1. When most DICY was attached with a single phosphorus-containing group of DOPO to produce a mixture comprising compounds (I) and (II), the phosphorus-containing group of DOPO provided a significant shift effect to the absorption of proton on —C(NH$_2$)$_2$ in the compound (I), however it only provided a slight shift effect to the absorption of proton on —C(NH$_2$)$_2$ in the compound (II). As the reaction was continued, another phosphorus-containing group would further attach with compound (II) and produce compound (III). Therefore, the absorption of proton on —C(NH$_2$)$_2$ was shifted from a range of δ6.65 ppm and δ6.69 ppm to around δ7.2 ppm due to a second phosphorus-containing group of DOPO like compound (I). Besides, if the second phosphorus-containing group of DOPO was attached onto the carbon which had already attached with the first phosphorus-containing group of DOPO (that is, two phosphorus-containing groups were attached onto the same carbon of —C≡N bond in DICY) and the carbon with two phosphorus-containing groups of DOPO were far from the proton on —C(NH$_2$)$_2$ in compound (II), the absorption of proton on —C(NH$_2$)$_2$ was hardly shifted by the phosphorus-containing groups of DOPO theoretically.

Furthermore, even if the absorption of proton on —C(NH$_2$)$_2$ would be shifted by two phosphorus-containing groups of DOPO attached onto the carbon of —C≡N bond, two absorptions of one single phosphorus-containing group of DOPO attached onto the carbon of —C≡N bond and of two phosphorus-containing groups of DOPO attached onto the carbon of —C≡N bond would respectively appear at two different positions with different chemical shifts in the $^1$H NMR spectrum. However, the aforementioned adsorptions were not found from the $^1$H NMR spectrum during the reaction process. It verified that a shift absorption of proton on —C(NH$_2$)$_2$ was mainly caused by the attachment of phosphorus-containing group of DOPO onto the carbon on C≡N double bond in DICY and by the formation of compound (I).

Hence, with reference to FIG. 2, a close intensity of the absorption of the proton at around δ7.2 ppm and in a range of δ6.65 ppm to δ6.69 ppm showed that a mixture comprising compounds (I) and (II) with a similar proportion was produced when DOPO was completely reacted with DICY with a molar ratio of 1:1 for 6 hours. However, it could not exclude that a little amount of compounds (III) were also produced by this reaction.

With reference to FIG. 5, compounds (I), (II), and (III) were respectively produced during the reaction. The absorption of the proton around δ7.2 ppm had been stronger than the absorption of the proton in the range from δ6.65 ppm to δ6.69 ppm when the reaction was being performed for 2 hours. It showed that a significant amount of compound (III) had been produced in the mixture.

Figure 6:
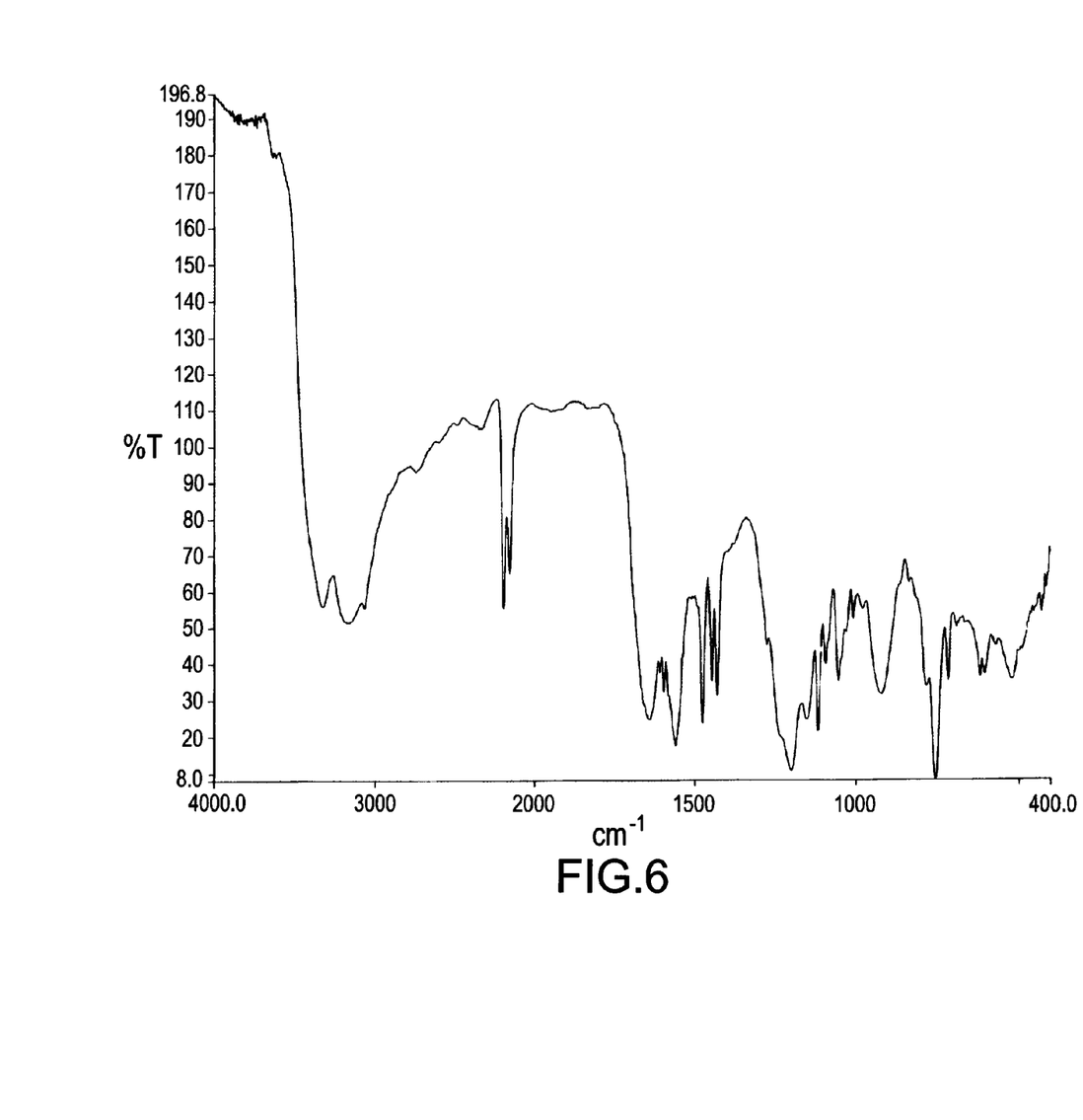
FIG. 6 is a FTIR spectrum of a mixture obtained from a reaction of DOPO and DICY with a molar ratio of 1.8:1 for 2 hours.

FIG. 6 illustrated a FTIR spectrum of a mixture obtained from a reaction of DOPO and DICY with a molar ratio of 1.8:1 for 2 hours. The mixture still had a quite apparent absorption peak of —C≡N bond in the range from 2150 cm$^{-1}$ to 2250 cm$^{-1}$, showing that a portion of —C≡N bond had not reacted with DOPO.

Figure 8A:
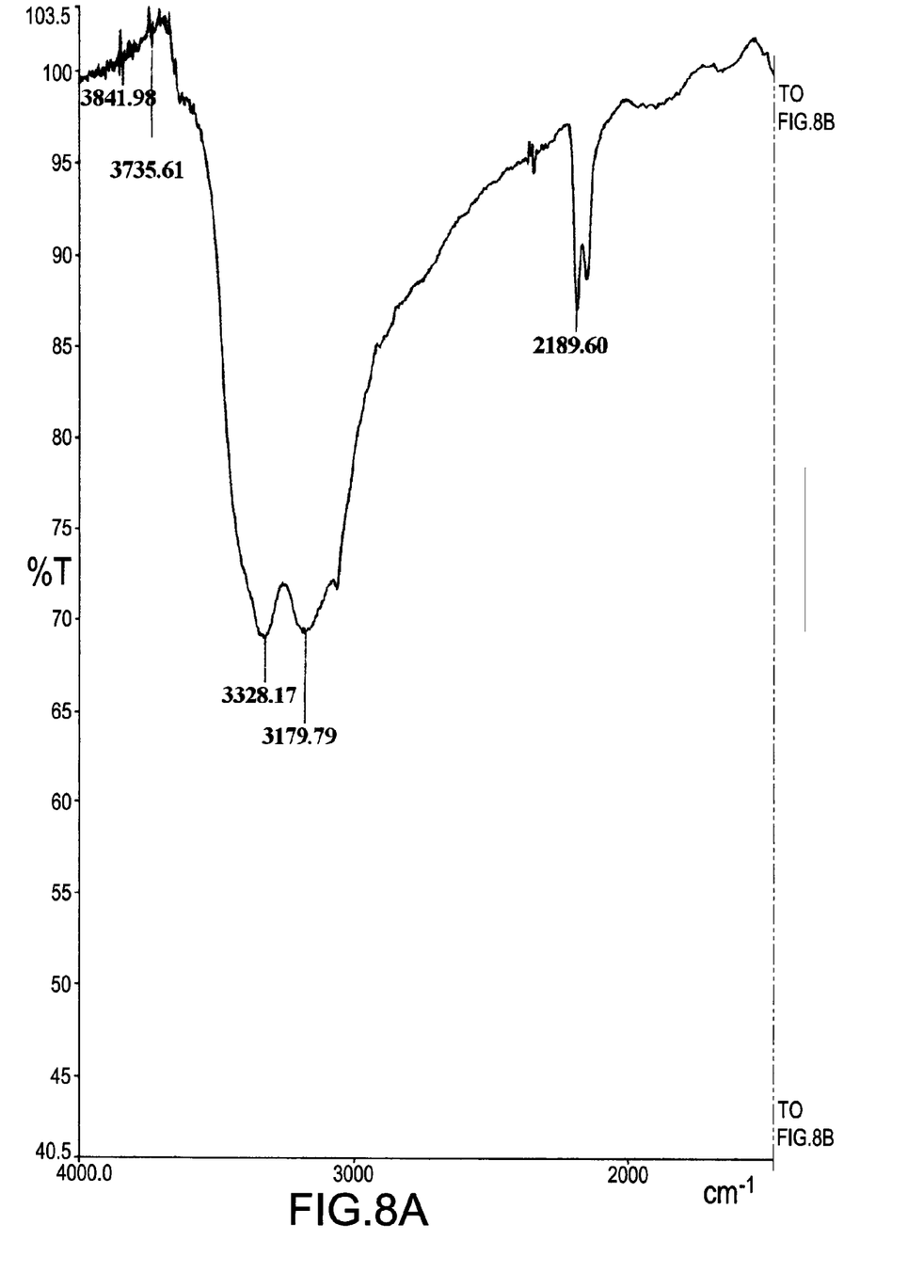
FIG. 8A is a portion of FTIR spectrum of a mixture obtained from a reaction of DOPO and DICY with a molar ratio of 1.8:1 for 8 hours (continued in FIG. 8B)
Figure 8B:
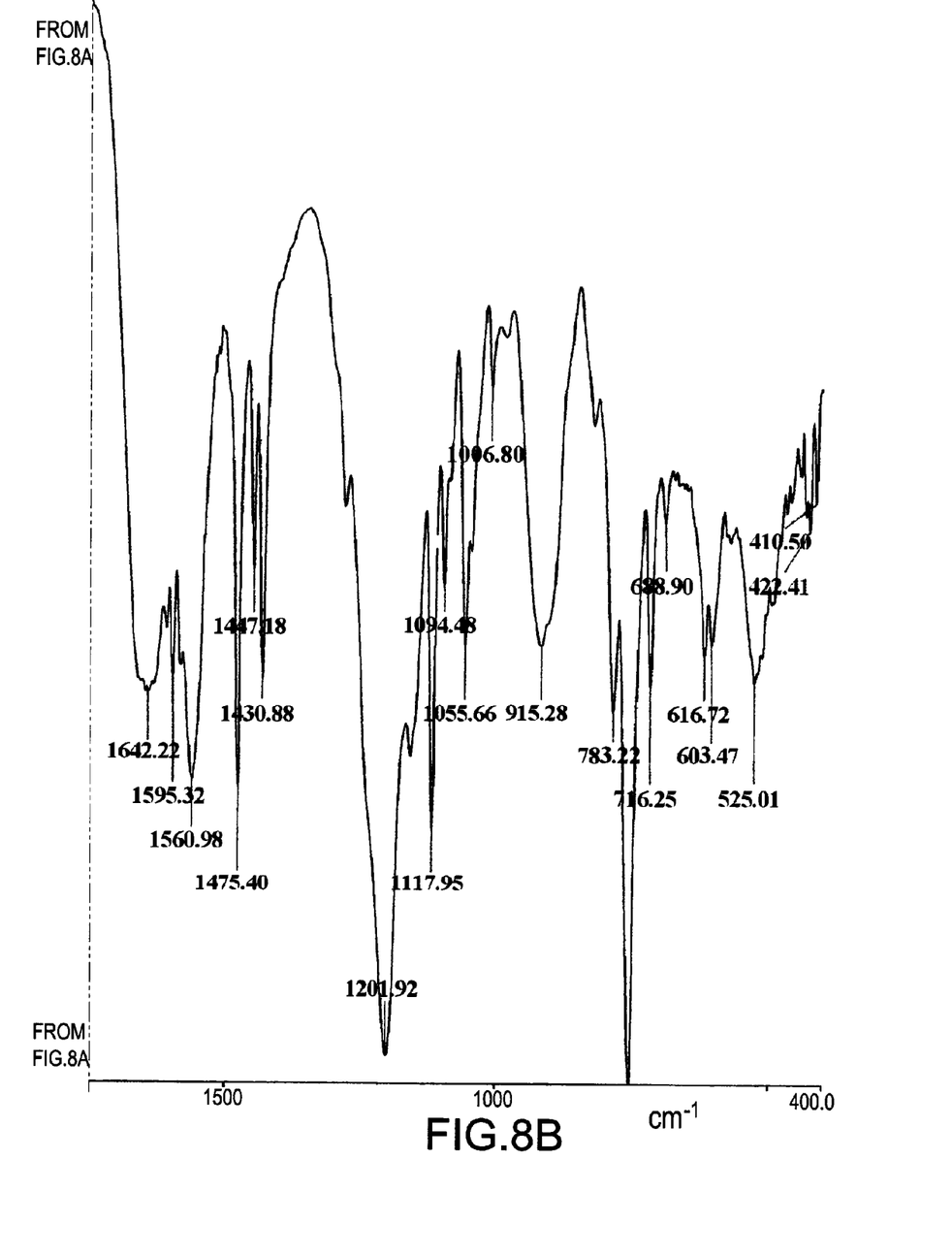
FIG. 8B is a portion of FTIR spectrum of a mixture obtained from a reaction of DOPO and DICY with a molar ratio of 1.8:1 for 8 hours (continued from FIG. 8A)

FIGS. 8A and 8B illustrated a FTIR spectrum of a mixture obtained from a reaction of DOPO and DICY with a molar ratio of 1.8:1 for 8 hours. The absorption peak of —C≡N bond in the range from 2150 cm$^{-1}$ to 2250 cm$^{-1}$ was still present but weaker in the FTIR spectrum. The result demonstrated once again that compound (III) was certainly the major compound in the mixture.

Figure 9:
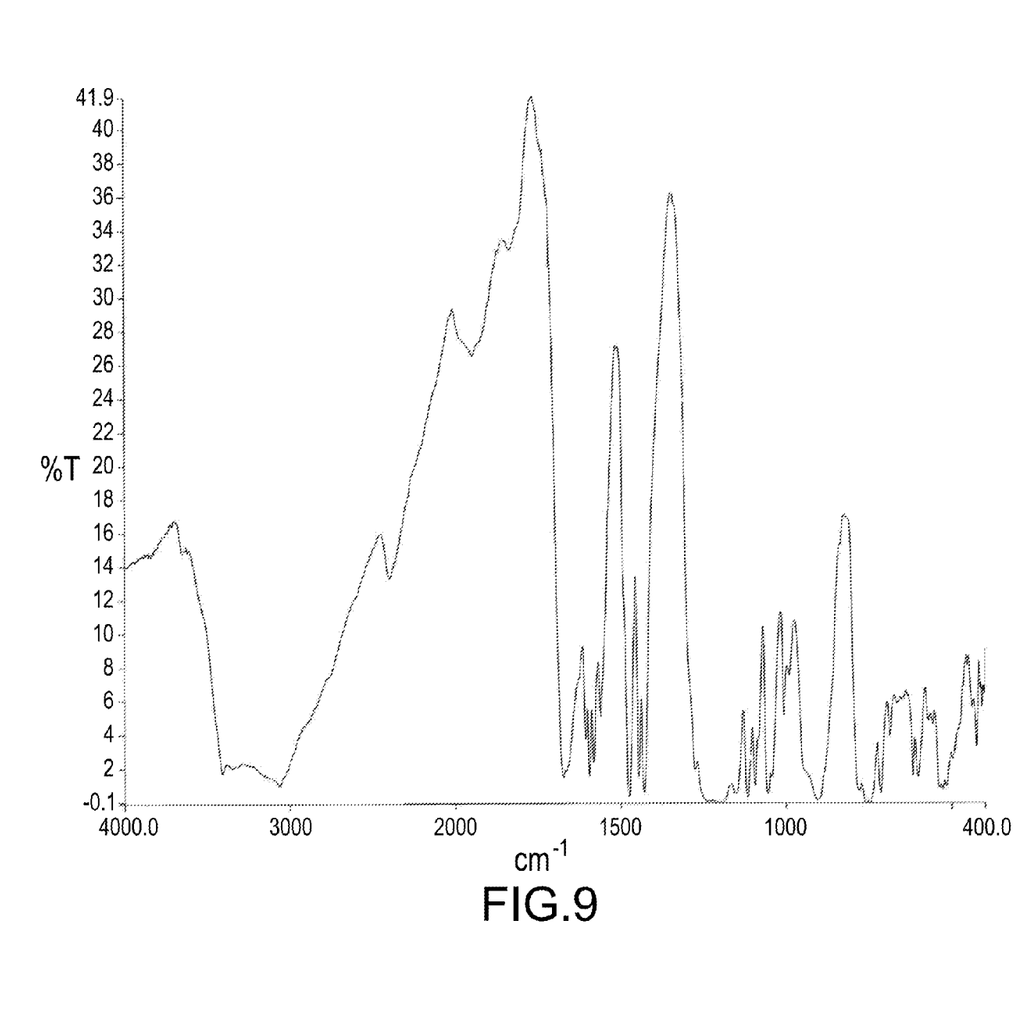
FIG. 9 is a FTIR spectrum of a mixture obtained from a reaction of DOPO and DICY with a molar ratio of 5:1 for 14 hours.

FIG. 9 illustrated a FTIR spectrum of a mixture obtained from a reaction of DOPO and DICY with a molar ratio of 5:1 for 14 hours. The absorption peak of —C≡N bond in the range from 2150 cm$^{-1}$ to 2250 cm$^{-1}$ disappeared. It demonstrated that every carbon on —C≡N bond of the DICY had respectively attached with a phosphorus-containing group of DOPO.

Test Example 2

Flame-Retardant Analysis of the Flame-Retardant Hardener for Epoxy Resin in Accordance with the Present Invention The products obtained from the aforementioned Preparation Example were further reacted with several resins to prepare a flame-retardant resin material in accordance with the present invention. The flame-retardant properties of the flame-retardant resin materials were determined by the following processes.

In the present example, the epoxy resins used were bisphenol A (BPA) epoxy resin, bisphenol A-Novolac epoxy resin (BNE) and o-cresol novolac epoxy resin (CNE), wherein both of the two latter resins were commercially available from Chang Chun Chemical Co., Ltd in Taiwan. Said three epoxy resins were respectively dissolved in acetone to obtain 70 wt % of epoxy resin solutions. Then, 70 wt % of epoxy resin solutions were reacted with the mixtures obtained from a reaction of DOPO and DICY with a molar ratio of 1:1 for 6 hours to produce the flame-retardant resin materials. Finally, a copper clad laminate made of the flame-retardant resin materials was obtained.

The flame-retardant properties of the copper clad laminate were determined by official standard flame-retardant UL-94 test. The amounts of reagents in Examples 1 to 6 were listed in Table 1. The chemical reagents of each example as shown in Table 1 were mixed with each other to prepare a varnish of the flame-retardant resin materials. Depending on different requirements, the varnish could be further added with an appropriate amount of 2-methylimidazole (2MI) (a promoting reagent) before impregnating a glass fiber cloth.

The methods of pressing the copper clad laminate were well known in the related arts and described as follows:

First, a glass fiber cloth of 20 cm in length and 20 cm in width (model name. TAIWANGLASS 2116) was impregnated with the varnish of the resin material, followed by being dried at a temperature ranging from 170° C. to 190° C. for 3 to 5 minutes to prepare a prepreg. Five sheets of the prepregs were obtained by the aforementioned process and followed by being laminated with two copper foils on the top and the bottom sides to prepare a pre-formed base. Subsequently, the pre-formed base was pressed under 20 kilograms/cm$^2$ at 170° C. to 190° C. for 50 minutes to 70 minutes to obtain a copper clad laminate. Finally, the copper foils formed on the surface of the copper clad laminate were removed to obtain a sample for flame-retardant analysis.

Examples 1 to 6 were tested by official flame-retardant UL-94 standard methods. Samples of copper clad laminate in Examples 1 and 2 were pressed at 175° C., and the samples of copper clad laminate in Examples 3 to 6 were pressed at 190° C. The flame-retardant results of Examples 1 to 6 were listed in Table 2. According to the flammability rating of official flame-retardant UL-94 standard method, the qualified ratings were classified into V-0, V-1, and V-2. As shown in Table 1, samples of Examples 1, 3, 4, 5 and 6 were determined as V-0, and the sample of Example 2 were determined as V-1.

TABLE 1 the amounts of chemical reagents such as resin, curing reagent, solvent in Examples 1~6 (unit: grams)

| Chemical reagents | Example 1 | Example 2 | Example 3 | Example 4 | Example 5 | Example 6 |
|---|---|---|---|---|---|---|
| CNE | 525.00 | — | 525.00 | — | — | 275.00 |
| BNE | — | 500.00 | — | 500.00 | — | — |
| BPA | — | — | — | — | 500.00 | 250.00 |
| Hardener - mixture of (I), (II), and (III) | 90.00 | 90.00 | 140.00 | 127.50 | 83.00 | 87.00 |
| DMF* | 200.00 | 200.00 | 200.00 | 200.00 | 200.00 | 180.00 |
| Al(OH)$_3$ | 180.00 | 180.00 | 180.00 | 180.00 | 190.00 | 190.00 |

DMF marked with * represents N,N-dimethylmethanamide

TABLE 2 the flame-retardant results of Examples 1~6 obtained by UL-94 method

| Test item | Example 1 | Example 2 | Example 3 | Example 4 | Example 5 | Example 6 |
|---|---|---|---|---|---|---|
| Flame Retardant | UL-94 V0 | UL-94 V1 | UL-94 V0 | UL-94 V0 | UL-94 V0 | UL-94 V0 |

The results demonstrated that the flame-retardant hardener for epoxy resin (a mixture comprising compounds (I), (II), and (III)) in accordance with the present invention could be mixed with resins to produce a standard qualified flame-retardant resin material based on the official flame-retardant UL-94 standards. Hence, the flame-retardant resin material could be used for replacing the halogenated resin material in a conventional curing process.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A flame-retardant hardener for epoxy resin having a compound represented by formula (I):

2. The flame-retardant hardener for epoxy resin as claimed in claim 1, wherein the flame-retardant hardener for epoxy resin further has a compound represented by formula (II):

3. The flame-retardant hardener for epoxy resin as claimed in claim 1, wherein the flame-retardant hardener for epoxy resin further has a compound represented by formula (III):

4. The flame-retardant hardener for epoxy resin as claimed in claim 1, wherein the flame-retardant hardener for epoxy resin further has compounds with structures represented by formulas (II) and (III):

(II)

(III)

5. A flame-retardant resin material comprising a flame-retardant hardener for epoxy resin as claimed in claim 1.

6. The flame-retardant resin material as claimed in claim 5, wherein the flame-retardant hardener for epoxy resin further has a compound represented by formula (II):

(II)

7. The flame-retardant resin material as claimed in claim 5, wherein the flame-retardant hardener for epoxy resin further has a compound represented by formula (III):

(III)

8. The flame-retardant resin material as claimed in claim 5, wherein the flame-retardant hardener for epoxy resin further has compounds with structures represented by formulas (II) and (III):

(II)

(III)

9. A method for manufacturing the flame-retardant hardener for epoxy resin as claimed in claim 1, comprising steps of:
  providing 9,10-dihydro-9-oxa-10-phosphaphenanthrene-10-oxide (DOPO) having a structure represented by formula (IV):

(IV)

heating DOPO until fully melted;
  providing dicyandiamide (DICY); and
  mixing DICY with DOPO to form a mixture, heating the mixture to undergo a reaction of DICY with DOPO, and cooling the mixture to obtain the flame-retardant hardener for epoxy resin.

10. The method as claimed in claim 9, wherein DOPO of the mixture has a mole number more than or equal to a mole number that DICY of the mixture has.

11. The method as claimed in claim 9, wherein the mixture is heated at a temperature higher than 130° C.

* * * * *